(12) United States Patent
Penna et al.

(10) Patent No.: US 10,925,607 B2
(45) Date of Patent: Feb. 23, 2021

(54) SURGICAL STAPLING APPARATUS WITH STAPLE SHEATH

(71) Applicant: Covidien LP, Mansfield, MA (US)

(72) Inventors: Christopher Penna, Guilford, CT (US); Stephen Ryan Casey, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 266 days.

(21) Appl. No.: 15/886,364

(22) Filed: Feb. 1, 2018

(65) Prior Publication Data

US 2018/0242975 A1    Aug. 30, 2018

Related U.S. Application Data

(60) Provisional application No. 62/464,627, filed on Feb. 28, 2017.

(51) Int. Cl.
| | | |
|---|---|---|
| *A61B 17/072* | (2006.01) | |
| *A61B 17/115* | (2006.01) | |
| *A61B 17/068* | (2006.01) | |
| *A61B 46/13* | (2016.01) | |

(Continued)

(52) U.S. Cl.
CPC ........ *A61B 17/1155* (2013.01); *A61B 17/068* (2013.01); *A61B 46/10* (2016.02); *A61B 46/13* (2016.02); *A61B 17/07292* (2013.01); *A61B 2017/00398* (2013.01); *A61B 2017/00473* (2013.01); *A61B 2017/07214* (2013.01); *A61B 2017/07271* (2013.01)

(58) Field of Classification Search
CPC ..... A61B 17/1155; A61B 46/10; A61B 46/13; A61B 17/068; A61B 2017/00473; A61B 17/07292; A61B 2017/00398; A61B 2017/07171; A61B 2017/07214
USPC ............................................ 227/175.1–182.1
See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |
| 3,124,136 A | 3/1964 | Usher |

(Continued)

FOREIGN PATENT DOCUMENTS

| | | |
|---|---|---|
| CA | 2282761 A1 | 9/1998 |
| DE | 1602563 U | 3/1950 |

(Continued)

OTHER PUBLICATIONS

Australian Examination Report No. 1 corresponding to AU 2014200793 dated Sep. 2, 2017.

(Continued)

*Primary Examiner* — Robert F Long
(74) *Attorney, Agent, or Firm* — Carter, DeLuca & Farrell LLP

(57) ABSTRACT

A cartridge assembly for selective connection to a surgical stapling apparatus includes a body portion, a tissue contact surface defining staple retention slots, staples, a collar assembly and a staple sheath. Each of the staples is received in a respective one of the staple retention slots of the tissue contact surface. The collar assembly is movably mounted to the body portion. The staple sheath is coupled to the collar assembly and positioned to cover the staple retention slots. The staple sheath is selectively movable relative to the tissue contact surface.

14 Claims, 11 Drawing Sheets

(51) Int. Cl.
  *A61B 46/10* (2016.01)
  *A61B 17/00* (2006.01)

(56) References Cited

U.S. PATENT DOCUMENTS

| | | |
|---|---|---|
| 3,364,200 A | 1/1968 | Ashton et al. |
| 3,490,675 A | 1/1970 | Green et al. |
| 3,499,591 A | 3/1970 | Green |
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,505,414 A * | 3/1985 | Filipi .................. A61B 17/115 227/155 |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,404,870 A * | 4/1995 | Brinkerhoff ........... A61B 17/00 227/175.1 |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |

(56) References Cited

U.S. PATENT DOCUMENTS

| | | |
|---|---|---|
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,303,106 B2 | 12/2007 | Milliman et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,625,209 B2 * | 12/2009 | Wade .................... A61C 1/16 408/56 |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,272,552 B2 | 9/2012 | Holsten et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |

(56) References Cited

U.S. PATENT DOCUMENTS

| | | |
|---|---|---|
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek (nee Prommersberger) et al. |
| 9,642,642 B2 * | 5/2017 | Lim .................. A61B 17/07207 |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 2001/0041899 A1 * | 11/2001 | Foster .................. A61B 17/221 606/127 |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0183671 A1 * | 10/2003 | Mooradian .......... A61B 17/115 227/175.1 |
| 2003/0208231 A1 | 11/2003 | Williamson et al. |
| 2003/0225419 A1 * | 12/2003 | Lippitt .................. A61B 17/221 606/127 |
| 2004/0092912 A1 | 5/2004 | Jinno et al. |
| 2004/0107006 A1 | 6/2004 | Francis et al. |
| 2004/0133418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0187576 A1 * | 8/2005 | Whitman ............ A61B 17/1155 606/219 |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |

(56) References Cited

U.S. PATENT DOCUMENTS

| | | |
|---|---|---|
| 2006/0229643 A1* | 10/2006 | Nolan ................. A61B 17/1114 606/153 |
| 2007/0034669 A1 | 2/2007 | de la Torre et al. |
| 2007/0051375 A1* | 3/2007 | Milliman ........... A61B 17/0218 128/856 |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0204108 A1* | 8/2009 | Steffen ................. A61B 17/068 606/1 |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0163598 A1* | 7/2010 | Belzer ................. A61B 17/115 227/181.1 |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0249805 A1* | 9/2010 | Olson ............... A61B 17/07207 606/144 |
| 2010/0331859 A1 | 12/2010 | Omori |
| 2011/0034910 A1 | 2/2011 | Ross et al. |
| 2011/0087279 A1* | 4/2011 | Shah ................. A61B 17/07207 606/219 |
| 2011/0089220 A1 | 4/2011 | Ingmanson et al. |
| 2011/0114699 A1 | 5/2011 | Baxter, III et al. |
| 2011/0118761 A1* | 5/2011 | Baxter, III ........... A61B 17/115 606/148 |
| 2011/0121049 A1 | 5/2011 | Malinouskas et al. |
| 2011/0125138 A1 | 5/2011 | Malinouskas et al. |
| 2011/0166673 A1 | 7/2011 | Patel et al. |
| 2011/0230897 A1* | 9/2011 | Palermo ................. A61B 17/10 606/142 |
| 2011/0248067 A1* | 10/2011 | Takei ................... A61B 17/115 227/175.1 |
| 2011/0293690 A1 | 12/2011 | Griffin et al. |
| 2012/0080336 A1 | 4/2012 | Shelton, IV et al. |
| 2012/0116416 A1 | 5/2012 | Neff et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2013/0153634 A1* | 6/2013 | Carter ................. A61B 17/1155 227/176.1 |
| 2013/0153636 A1 | 6/2013 | Shelton, IV et al. |
| 2013/0153639 A1* | 6/2013 | Hodgkinson ........ A61B 17/068 227/180.1 |
| 2013/0153641 A1 | 6/2013 | Shelton, IV et al. |
| 2013/0209659 A1 | 8/2013 | Racenet et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0217148 A1* | 8/2014 | Penna ............... A61B 17/07292 227/179.1 |
| 2014/0224686 A1* | 8/2014 | Aronhalt ............. A61B 17/068 206/339 |
| 2014/0239047 A1 | 8/2014 | Hodgkinson et al. |
| 2014/0252062 A1* | 9/2014 | Mozdzierz ....... A61B 17/07292 227/175.1 |
| 2015/0041347 A1 | 2/2015 | Hodgkinson |
| 2015/0133995 A1 | 5/2015 | Shelton, IV et al. |
| 2015/0157320 A1 | 6/2015 | Zergiebel et al. |
| 2015/0173757 A1* | 6/2015 | Williams ........... A61B 17/1155 227/180.1 |
| 2015/0209045 A1 | 7/2015 | Hodgkinson et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0157857 A1 | 6/2016 | Hodgkinson et al. |
| 2016/0174988 A1 | 6/2016 | D'Agostino et al. |
| 2016/0192934 A1 | 7/2016 | Williams et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0256166 A1 | 9/2016 | (Prommersberger) Stopek et al. |
| 2016/0270793 A1 | 9/2016 | Carter et al. |
| 2016/0310143 A1 | 10/2016 | Bettuchi |
| 2016/0324525 A1* | 11/2016 | Scheib ............... A61B 17/1155 |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2019/0343521 A1* | 11/2019 | Williams ......... A61B 17/07292 |

FOREIGN PATENT DOCUMENTS

| | | |
|---|---|---|
| DE | 19924311 A1 | 11/2000 |
| EP | 0 327 022 A2 | 8/1989 |
| EP | 0 594 148 A1 | 4/1994 |
| EP | 2 491 867 A1 | 8/2012 |
| EP | 2730237 A1 | 5/2014 |
| JP | 2000-166933 A | 6/2000 |
| JP | 2002-202213 A | 7/2002 |
| JP | 2007-124166 A | 5/2007 |
| JP | 2010-214132 A | 9/2010 |
| WO | 90/05489 A1 | 5/1990 |
| WO | 95/16221 A1 | 6/1995 |
| WO | 98/38923 A1 | 9/1998 |
| WO | 99/26826 A2 | 6/1999 |
| WO | 00/10456 A1 | 3/2000 |
| WO | 00/16684 A1 | 3/2000 |
| WO | 2009/039506 A1 | 3/2009 |
| WO | 2010/075298 A2 | 7/2010 |
| WO | 2011087848 A1 | 7/2011 |
| WO | 2016/025132 A1 | 2/2016 |

OTHER PUBLICATIONS

Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.

(56) References Cited

OTHER PUBLICATIONS

Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
European Office Action corresponding to EP 14 17 2681.0 dated May 13, 2016.
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).

(56) References Cited

OTHER PUBLICATIONS

European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 58425, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.

(56) References Cited

OTHER PUBLICATIONS

Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
Partial European Search Report issued in European Application No. 18158993.8 dated Oct. 16, 2018.

* cited by examiner

SURGICAL STAPLING APPARATUS WITH STAPLE SHEATH

CROSS-REFERENCE TO RELATED APPLICATIONS

This application claims the benefit of and priority to U.S. Provisional Patent Application Ser. No. 62/464,627 filed Feb. 28, 2017, the entire disclosure of which is incorporated by reference herein.

TECHNICAL FIELD

The present disclosure relates to surgical stapling apparatus for performing endoscopic surgical procedures and methods of use thereof.

BACKGROUND

Fasteners, e.g., staples or two-part fasteners, have traditionally been used to replace suturing when joining various body structures such as the bowel or bronchus, for instance. Surgical stapling apparatus employed to apply these fasteners are generally designed to clamp, cut and/or fasten tissue between opposing jaw structure. Circular surgical stapling apparatus, for example, generally include an annular fastener cartridge assembly that supports annular rows of fasteners in fastener retaining slots, an annular anvil assembly with fastener forming pockets for forming the fasteners of the fastener cartridge upon a firing of the circular surgical stapling apparatus, and an annular blade for cutting tissue. These circular surgical stapling apparatus sequentially or simultaneously apply these fasteners to tissue for the purpose of joining segments of tissue together and/or for the creation of anastomoses.

One challenge associated with anastomosis procedures includes maintaining the integrity of the anastomosis. During instrument insertion into a surgical site, there is a risk that contaminants in proximity to the surgical site could migrate into the fastener retaining slots of the fastener cartridge and contaminate the fasteners supported therein.

Accordingly, it would be advantageous to provide a surgical stapling apparatus that prevents fastener contamination for improving the integrity of an anastomosis.

SUMMARY

According to an aspect of the present disclosure, a surgical stapling apparatus is provided. The surgical stapling apparatus includes a first jaw member, staples, a second jaw member and a staple sheath. The first jaw member has staple retention slots. Each staple is received in a respective one of the staple retention slots. The second jaw member has staple pockets. Each staple pocket is configured to form a respective one of the staples of the plurality of staples as the surgical stapling apparatus is fired. The staple sheath is secured to the first jaw member and covers the staple retention slots. The staple sheath is movable relative to the first jaw member to uncover the staple retention slots in response to relative approximation of the first jaw member and the second jaw member.

In some embodiments, the staple sheath may be part of a staple sheath assembly including a collar assembly and the staple sheath coupled to the collar assembly.

In embodiments, the second jaw member may include a head assembly having a center rod assembly extending proximally from the head assembly. The center rod assembly may be selectively engagable with the collar assembly to move the staple sheath relative to the first jaw member to uncover the plurality of staple retention slots in response to relative approximation of the first jaw member and the second jaw member.

In some embodiments, the collar assembly may include one or more spokes and the first jaw member may define one or more elongated channels that extend axially along the first jaw member. The one or more spokes may be slidably movable through the one or more elongated channels to enable the staple sheath to move relative to the first jaw member.

In certain embodiments, the first jaw member may include a staple cartridge. The staple cartridge may define an annular groove configured to receive a distal end portion of the staple sheath assembly to selectively secure the staple sheath across the staple cartridge covering the staple retention slots while the first and second jaw members are unapproximated.

In some embodiments, the surgical stapling apparatus further includes an elongated shaft assembly that extends from a proximal end portion to a distal end portion. The first jaw member and the staple sheath assembly may be removably secured to the distal end portion of the elongated shaft assembly.

According to another aspect of the present disclosure, an end effector for a surgical stapling apparatus is provided. The end effector includes a cartridge assembly, staples, an anvil assembly, and a staple sheath. The cartridge assembly has staple retention slots. Each staple is received in a respective one of the staple retention slots. The anvil assembly has staple pockets. Each staple pocket is configured to form a respective one of the staples as the surgical stapling apparatus is fired. The anvil assembly is movable relative to the cartridge assembly between an unapproximated position and an approximated position. The staple sheath is secured to the cartridge assembly and positioned to cover the staple retention slots. The staple sheath is movable with the anvil assembly to uncover the plurality of staple retention slots and expose the plurality of staples.

In certain embodiments, the anvil assembly may include a head assembly and a center rod assembly that extends from the head assembly. The center rod assembly may be selectively engagable with the collar assembly to move the staple sheath relative to the cartridge assembly upon a movement of the anvil assembly relative to the cartridge assembly.

In embodiments, the collar assembly may include one or more spokes and the cartridge assembly defines one or more elongated channels extending axially along the cartridge assembly. The one or more spokes may be slidably movable through the one or more elongated channels to enable the staple sheath to move relative to the cartridge assembly.

In some embodiments, the cartridge assembly may include a staple cartridge defining an annular groove configured to receive a distal end portion of the staple sheath assembly to selectively secure the staple sheath in a position to cover the plurality of staple retention slots while the anvil and cartridge assemblies are in the unapproximated position.

In certain embodiments, the end effector further includes an elongated shaft assembly that extends from a proximal end portion to a distal end portion. The cartridge assembly and the staple sheath assembly may be removably secured to the distal end portion of the elongated shaft assembly.

According to yet another aspect of the present disclosure, a circular stapling apparatus is provided. The circular stapling apparatus includes an elongated shaft assembly, a cartridge assembly, staples, a collar assembly, and a staple sheath. The elongated shaft assembly has a distal end portion and defining a longitudinal axis. The cartridge assembly is secured to the distal end portion of the elongated shaft assembly and has a tissue contact surface. The tissue contact surface defines staple retention slots. Each staple is received in a respective one of the staple retention slots. The collar assembly is movable along the longitudinal axis between a distal position and a proximal position. The staple sheath is coupled to the collar assembly and positioned to cover the plurality of staple retention slots while the collar assembly is in the distal position. The staple sheath is movable with the collar assembly toward the proximal position to draw the staple sheath across the plurality of staple retention slots.

In some embodiments, the collar assembly may include one or more spokes and the cartridge assembly may define one or more elongated channels extending axially along the cartridge assembly. The one or more spokes may be slidably movable through the one or more elongated channels to enable the staple sheath to move relative to the cartridge assembly.

In certain embodiments, the cartridge assembly may include a staple cartridge defining an annular groove configured to receive a distal end portion of the staple sheath to selectively secure the staple sheath in a position to cover the staple retention slots.

In some embodiments, the cartridge assembly and the staple sheath assembly may be selectively removable from the distal end portion of the elongated shaft assembly.

In embodiments, the circular stapling apparatus may further include an anvil assembly selectively coupled to the elongated shaft assembly. The anvil assembly may be movable relative to the cartridge assembly to move the collar assembly from the distal position to the proximal position.

According to still another aspect of the present disclosure, a cartridge assembly for selective connection to a surgical stapling apparatus is provided. The cartridge assembly includes a body portion, a tissue contact surface, staples, a collar assembly, and a staple sheath. The tissue contact surface defines staple retention slots. Each staple is received in a respective one of the staple retention slots. The collar assembly is movably mounted to the body portion. The staple sheath is coupled to the collar assembly and positioned to cover the staple retention slots. The staple sheath is selectively movable relative to the tissue contact surface.

In some embodiments, the body portion defines one or more elongated channels. The collar assembly may include one or more spokes slidably movable through the one or more elongated channels to enable the staple sheath to move relative to the body portion.

In certain embodiments, the cartridge assembly further includes a staple cartridge coupled to the body portion. The staple cartridge may include the tissue contact surface and may support the staples. The staple cartridge may define an annular groove configured to receive a distal end portion of the staple sheath to selectively secure the staple sheath across the tissue contact surface of the staple cartridge.

In embodiments, the collar assembly may be is selectively movable between distal and proximal positions relative to the body portion to move the staple sheath relative to the tissue contact surface.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
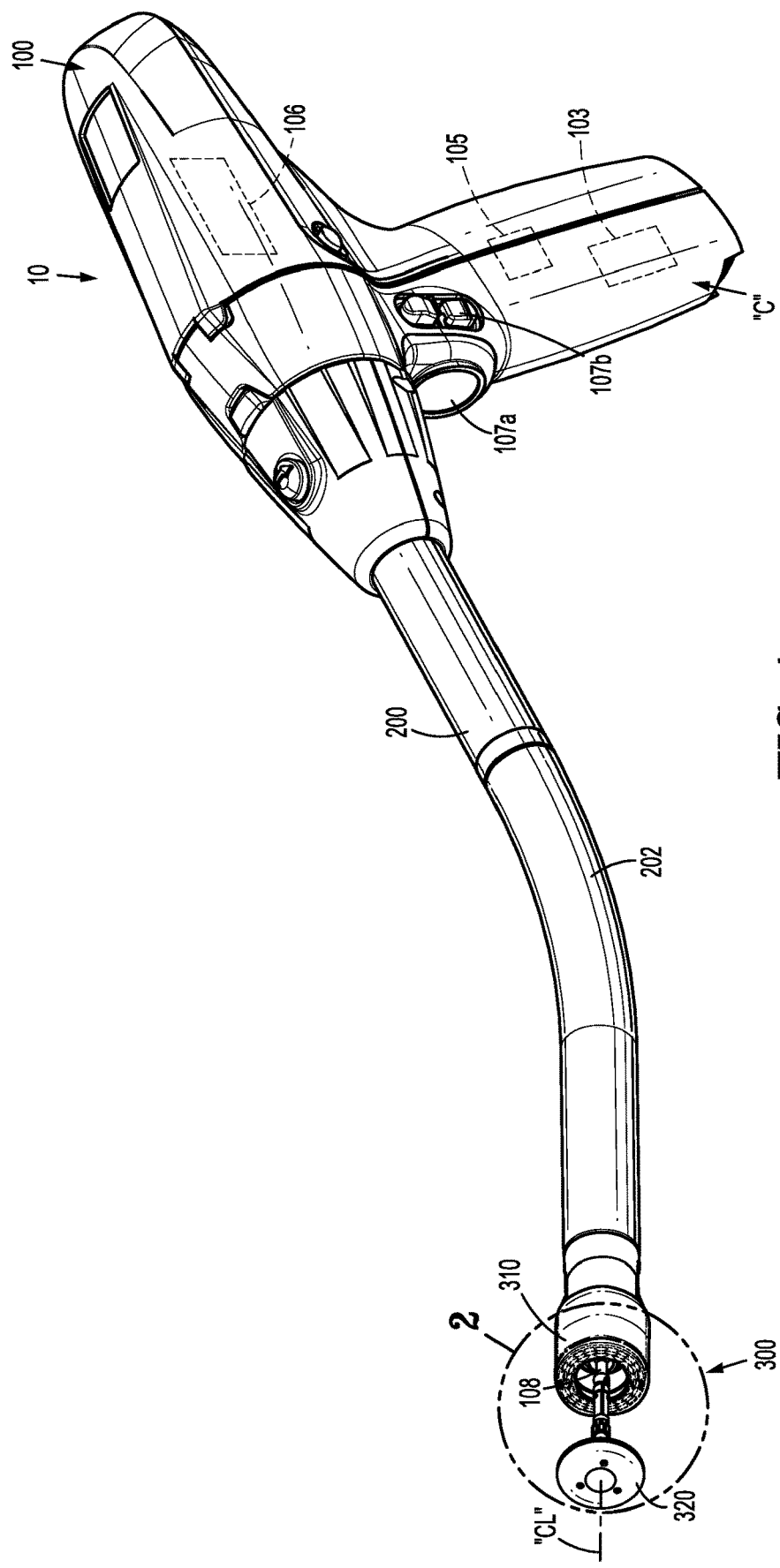
FIG. 1 is a perspective view of a surgical stapling apparatus in accordance with the principles of the present disclosure.

Embodiments of the presently disclosed surgical stapling apparatus are described in detail with reference to the drawings, in which like reference numerals designate identical or corresponding elements in each of the several views. As used herein, the term "distal" refers to that portion of the apparatus, and/or component thereof, farther from the user, while the term "proximal" refers to that portion of the apparatus, and/or component thereof, closer to the user. As used herein, the term "clinician" refers to a doctor, nurse, or other care provider and may include support personnel. In the following description, well-known functions or constructions are not described in detail to avoid obscuring the present disclosure in unnecessary detail.

Figure 2:
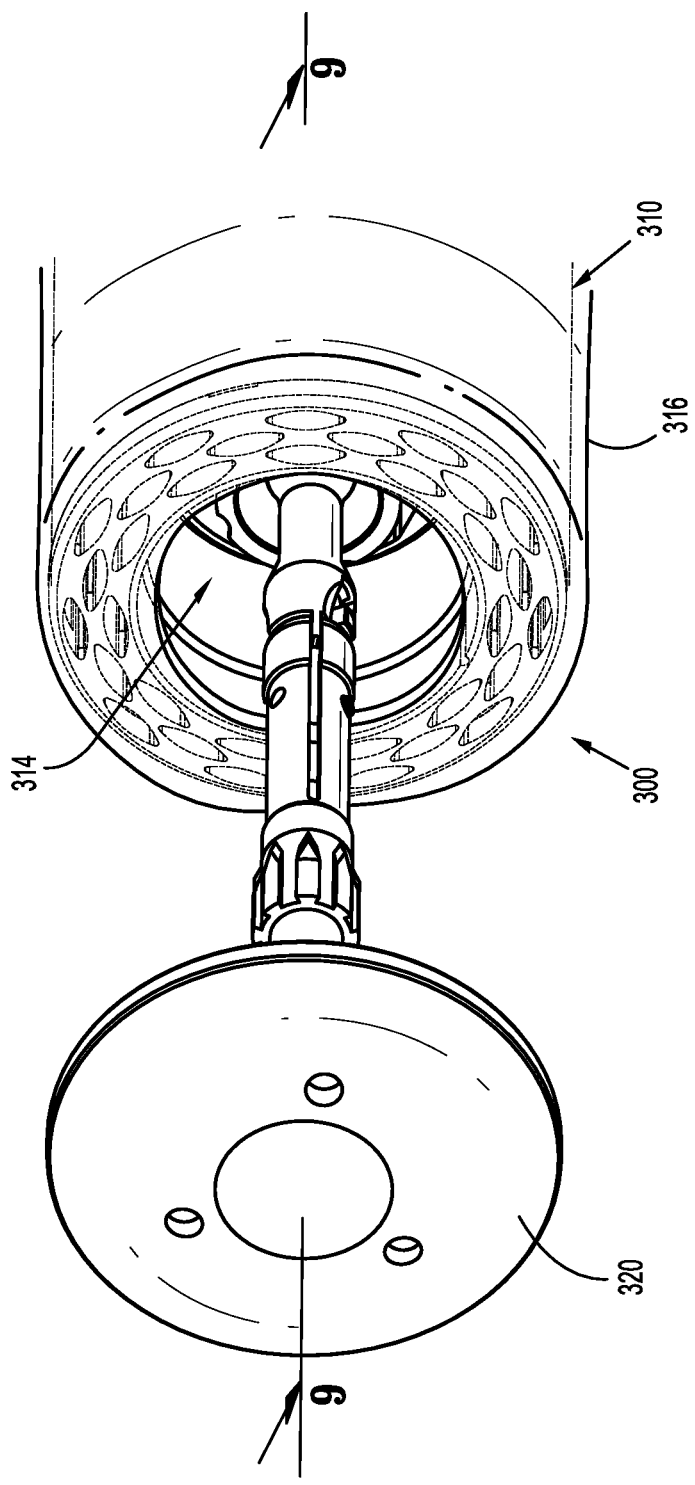
FIG. 2 is an enlarged, perspective view of an end effector of the surgical stapling apparatus of FIG. 1 with an anvil assembly of the end effector shown unapproximated from a cartridge assembly of the end effector.

Turning now to FIGS. 1 and 2, an electromechanical surgical stapling system or apparatus, generally referred to as 10, defines a centerline "CL" and includes a surgical device 100 in the form of a powered handheld electromechanical instrument. The electromechanical surgical stapling system 10 further includes an adapter assembly 200 that is selectively attachable to the surgical device 100. The adapter assembly 200 extends distally from the surgical device 100 and has an elongated body 202 that extends to a distal end. The distal end of the elongated body 202 supports an end effector 300. The end effector 300 includes a shell or cartridge assembly 310 and an anvil assembly 320 that are positionable between an unclamped or unapproximated position (see FIG. 1) and a clamped or approximated position (see FIG. 12) to selectively clamp tissue (not shown) for cutting and/or stapling the tissue. The surgical device 100 is configured for selective connection with the adapter assembly 200, and, in turn, the adapter assembly 200 is configured for selective connection with the end effector 300. Together, the surgical device 100 and the adapter assembly 200 cooperate to operate the end effector 300.

In some embodiments, the surgical device 100 of the electromechanical surgical stapling system 10 includes a handle housing 102 that defines a cavity "C" for selective removable receipt of a rechargeable battery 103. The battery 103 is configured to supply power to electrical components of the surgical device 100. The cavity "C" supports a controller or circuit board 105 configured to control various operations of the surgical device 100.

The electromechanical surgical stapling system 10 further includes a drive mechanism 106 configured to drive rotatable shafts and/or gear components (not shown) within the handle housing 102 in order to perform various operations of the electromechanical surgical stapling system 10. For instance, the drive mechanism 106 may be operable to selectively rotate the end effector 300 about, and/or relative to, the centerline "CL" of the electromechanical surgical stapling system 10; to selectively move the anvil assembly 320 relative to the cartridge assembly 310 to selectively clamp tissue; and/or to fire the electromechanical surgical stapling system 10 for fastening and/or cutting the clamped tissue. The battery 103, controller 105, and/or drive mechanism 106 may be operably coupled to one or more triggers 107a, 107b such as finger-actuated control buttons, rocker devices, and/or the like to effectuate various functions of the electromechanical surgical stapling system 10 such as those described above.

The drive mechanism 106 of the electromechanical surgical stapling system 10 includes an approximation mechanism 108 that extends distally through the elongated body 202 and includes an anvil retainer 108a (FIG. 9) supported on a distal end portion of the approximation mechanism 108. The anvil retainer 108a is configured to move along the centerline "CL" of the electromechanical surgical stapling system 10 between distal and proximal positions to selectively or removably couple to the anvil assembly 320 as described in U.S. Pat. No. 7,303,106, the entire contents of which are incorporated by reference herein. The anvil retainer 108a is also configured to move along the centerline "CL" of the electromechanical surgical stapling system 10 between the distal and proximal positions of the anvil retainer 108a to move the anvil assembly 320 between the approximated and unapproximated positions relative to the cartridge assembly 310 to selectively clamp and/or unclamp tissue.

Reference may be made to International Application No. PCT/US2008/077249, filed Sep. 22, 2008 (Inter. Pub. No. WO 2009/039506), U.S. Patent Application 2015/0157320, filed Nov. 21, 2014, and U.S. Patent Application Publication No. 2011/0121049, filed on Nov. 20, 2009, the entire contents of each of which are incorporated herein by reference, for a detailed description of the construction and operation of various exemplary electromechanical surgical systems, the components of which are combinable and/or interchangeable with one or more components of electromechanical surgical systems 10 described herein.

Although the surgical stapling apparatus is described as an electromechanically powered surgical stapling apparatus, the presently disclosed surgical stapling apparatus can be provided as a manually powered stapling apparatus. For a more detailed description of the construction and operation of an exemplary manually powered stapling apparatus, one or more components of which can be combined and/or interchanged with the electromechanically powered stapling apparatus described herein, reference can be made to U.S. Pat. No. 8,272,552, filed Jan. 30, 2012, the entire contents of which are incorporated by reference herein (see also U.S. Pat. No. 7,303,106 incorporated herein by reference above).

Figure 3:
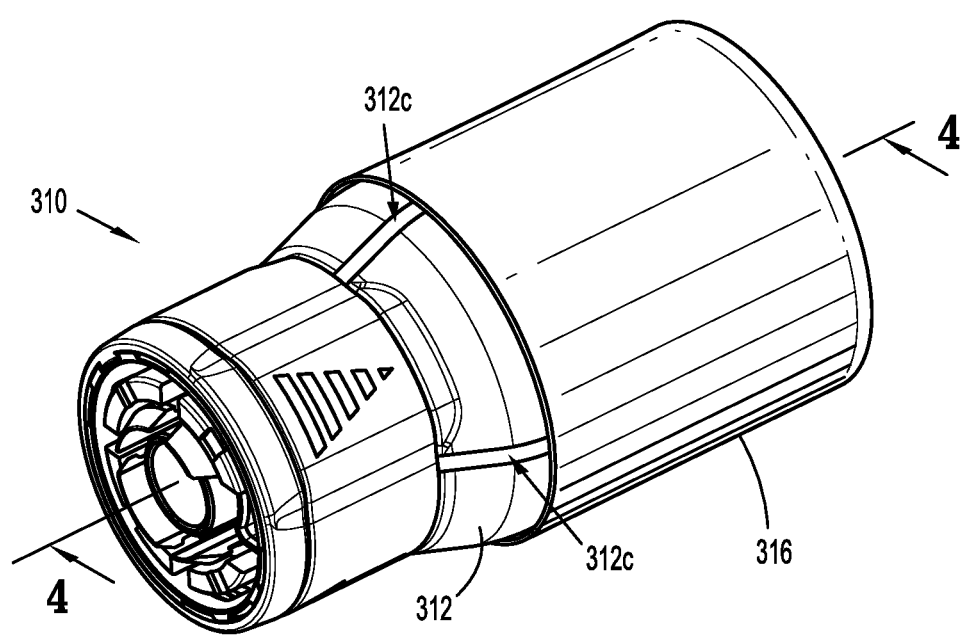
FIG. 3 is a perspective view of the cartridge assembly of FIG. 2 with a staple sheath assembly of the cartridge assembly shown in a first position.
Figure 4:
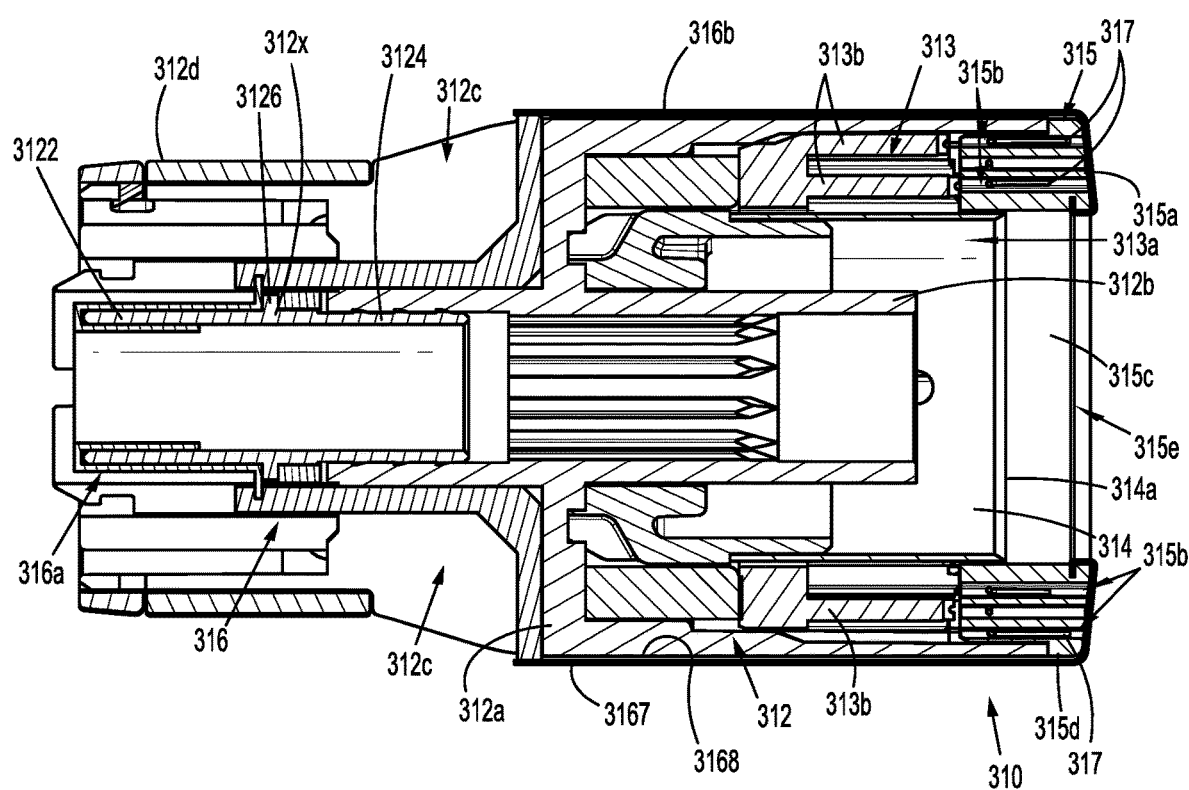
FIG. 4 is cross-sectional view of the cartridge assembly of FIG. 3 as taken along section line 4-4 of FIG. 3.

Turning now to FIGS. 3 and 4, the cartridge assembly 310 of the end effector 300 includes a shell 312, a pusher 313, a cylindrical knife 314, a staple cartridge 315, and a staple sheath assembly 316.

The shell 312 of the cartridge assembly 310 is secured to a distal end of the elongated body 202 of the adapter assembly 200 and includes an outer housing portion 312a configured to selectively receive the staple cartridge 315, an inner guide portion 312b configured to selectively receive the anvil assembly 320 of the end effector 300, and a coupling portion 312x configured to couple the cartridge assembly 310 to the elongated body 202 of the adapter assembly 200. The coupling portion 312x includes a proximal portion 3122, a distal portion 3124, and a flange 3126 that separates the proximal and distal portions 3122, 3124. The outer housing portion 312a defines elongated slots 312c at radially spaced locations around the shell 312 and which are configured to slidably support the staple sheath assembly 316. The outer housing portion 312a includes a housing collar assembly 312d configured to facilitate selective attachment of the cartridge assembly 310 to the elongated body 202 similar to that described in U.S. Patent Application Publication No. 2016/0192934, filed Oct. 19, 2015, the entire contents of which are incorporated by reference herein.

The pusher 313 of the cartridge assembly 310 is slidably positioned about the inner guide portion 312b of the shell 312 and defines a central throughbore 313a. The pusher 313 includes annular arrays of distally extending fingers 313b configured to support an array of staples 317. One or more of the fingers 313b and/or one or more of the staples 317 may include different heights. In some embodiments, one or more of the fingers 313b and/or one or more of the staples 317 may include the same height.

The cylindrical knife 314 of the cartridge assembly 310 is frictionally retained within the central throughbore 313a of the pusher 313 to fixedly secure the knife 314 in relation to the pusher 313. The distal end of the knife 314 includes a circular cutting edge 314a configured to severe tissue.

The staple cartridge 315 of the cartridge assembly 310 includes a tissue contact surface 315a in which annular arrays of slots 315b are formed. The annular arrays of slots 315b of the staple cartridge 315 are configured to support and slidably receive the annular arrays of staples 317 therein. The staple cartridge 315 includes an inner surface 315c and an outer surface 315d. The inner surface 315c defines a groove 315e therein. The groove 315e of the inner surface 315c of the staple cartridge 315 may have an annular configuration.

Figure 5:
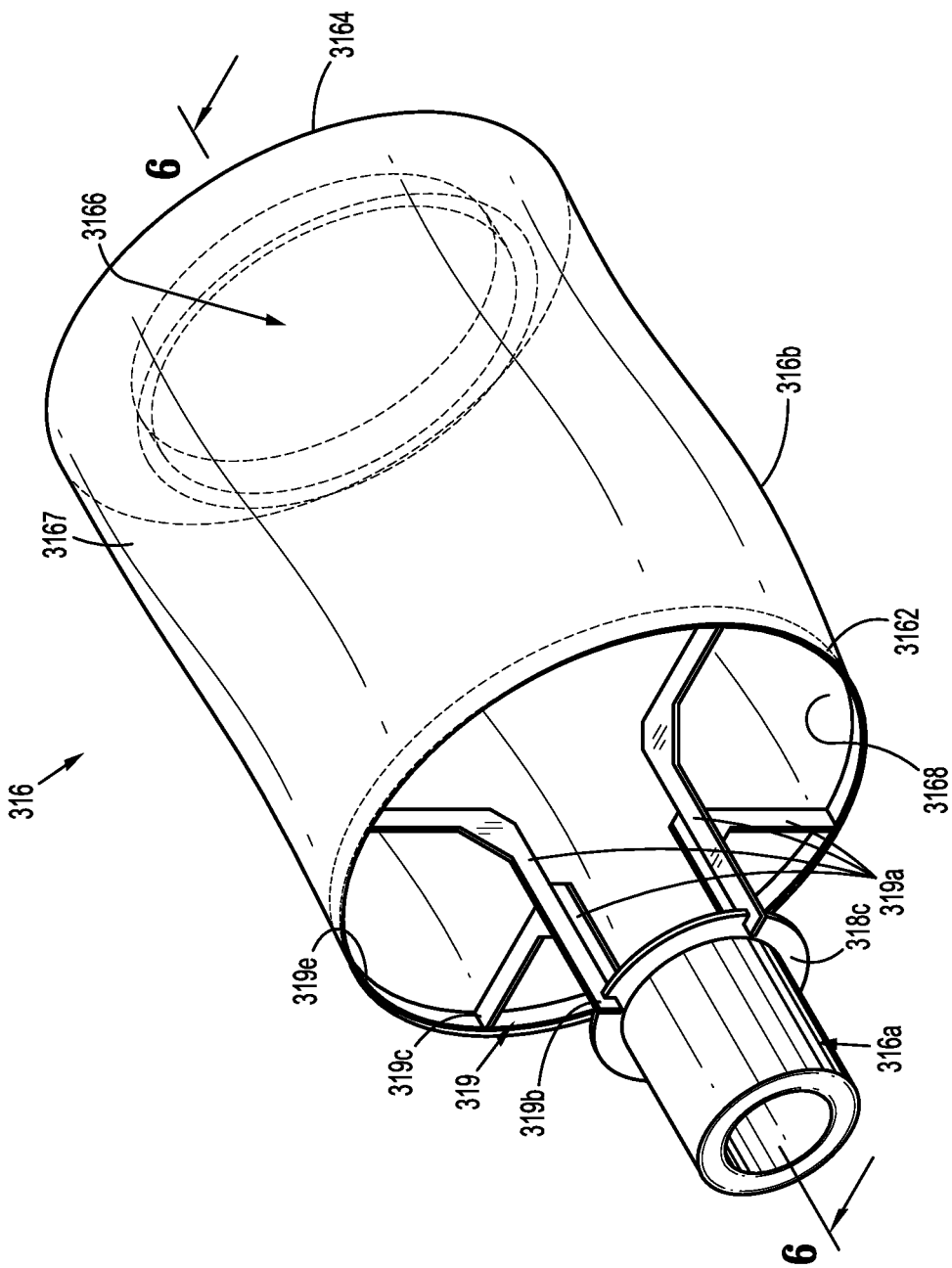
FIG. 5 is a perspective view of the staple sheath assembly shown in FIG. 3.
Figure 6:
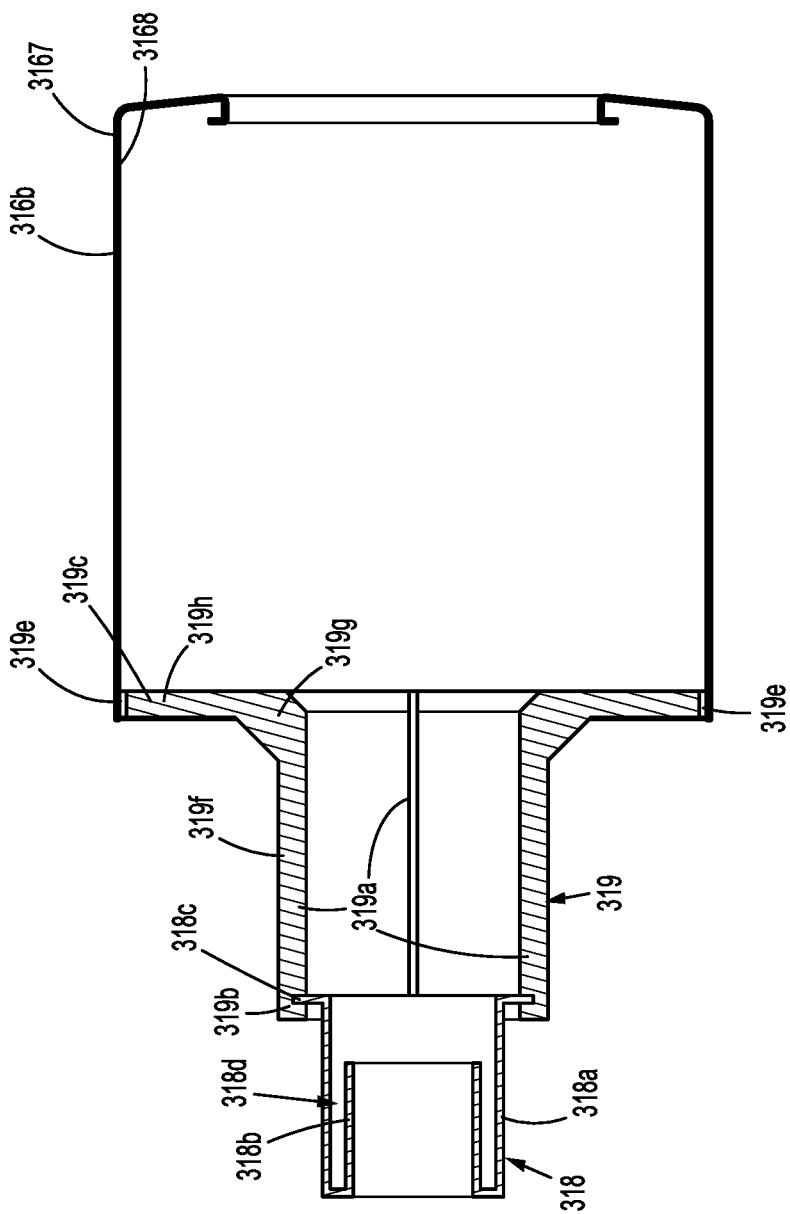
FIG. 6 is a cross-sectional view of the staple sheath assembly of FIG. 5 as taken along section line 6-6 of FIG. 5.

With reference to FIGS. 5 and 6, the staple sheath assembly 316 of the cartridge assembly 310 includes a collar assembly 316a coupled to a staple sheath 316b.

The staple sheath 316b of the staple sheath assembly 316 includes a proximal end portion 3162, a distal end portion 3164, and an opening 3166 defined through the proximal and distal end portions 3162, 3164 of the staple sheath 316b. The staple sheath 316b further includes an outer surface 3167 and an inner surface 3168. The proximal end portion 3162 of the staple sheath 316b is secured to the collar assembly 316a and the distal end portion 3164 of the staple sheath 316b is receivable within the groove 315e of the staple cartridge 315 to selectively or removably secure the distal end portion 316d of the staple sheath 316b to the staple cartridge 315. The distal end portion 316d of the staple sheath 316b may be folded over the tissue contact surface 315a of the staple cartridge 315 and/or folded into the groove 315e of the staple cartridge 315. The staple sheath 316b is configured to cover the tissue contact surface 315a, annular arrays of slots 315b, and annular arrays of staples 317 of the staple cartridge 315 while the distal end portion 316d is secured to the groove 315e of the staple cartridge 315 to protect and maintain sterility of the staple cartridge 315 and staples 317. The staple sheath 316b is also configured to move relative to the staple cartridge 315 to separate the staple sheath 316b from the groove 315e and slide along the tissue contact surface 315a of the staple cartridge 315.

In some embodiments, the staple sheath 316b, or portions thereof, can be configured to be drawn across the staple cartridge 315 to expose the tissue contact surface 315a and the staples 317. In certain embodiments, the staple sheath 316b can be configured to be drawn partially across the tissue contact surface 315a of the staple cartridge 315. In some embodiments, the staple sheath 316, or portions thereof, may be configured to act as buttress material that remains coupled to the staple cartridge 315 until secured to tissue with the staples 317 upon a firing of the staples 317 from the staple cartridge 315. For example, the distal end portion 316d of the staple sheath 316b may be separated from the groove 315e of the staple cartridge 315 and drawn across the tissue contact surface 315a such that the distal end portion 316d covers the tissue contact surface 315a and acts as a buttress material for use with the staples 317.

In some embodiments, the distal end portion 316d of the staple sheath 316 is configured to remain fixed to the groove 315e of the staple cartridge 315 such that movement of the staple sheath 316b relative to the staple cartridge 315 causes the staple sheath 316b to tear, dividing the staple sheath 316b into separate portions. In certain embodiments, the staple sheath 316, or portions thereof, may include perforations (e.g., an annular ring of perforations, not shown) or the like, to enable portions of the staple sheath 316 to separate from one another upon an application of separating force thereto. In certain embodiments, the staple sheath 316, or portions thereof, may be formed in bands, layers, and/or combinations thereof.

The staple sheath 316b, or portions thereof, may be formed of any suitable polymeric material. The polymeric material may be flexible. In some embodiments, the staple sheath 316b may include multiple materials. In embodiments, the staple sheath 316b, or portions thereof, may include biocompatible and/or biodegradable material. In some embodiments, the staple sheath 316b may include biologically acceptable additives such as plasticizers, antioxidants, dyes, dilutants, therapeutic agents, and the like, and/or combinations thereof, which can be coated thereon, and/or impregnated therein (e.g., during formation). For a more detailed description of suitable materials and/or additives for use with the staple sheath of the present disclosure, reference can be made to U.S. Pat. No. 8,453,910, the entire contents of which are incorporated by reference herein.

The collar assembly 316a of the staple sheath assembly 316 includes a first or proximal collar 318 coupled to a second or distal collar 319. The proximal collar 318 of the collar assembly 316a includes an outer member 318a, an inner member 318b coupled to the outer member 318a, and an annular flange 318c extending radially outward from a distal end of the outer member 318a to couple the proximal and distal collars 318, 319 together. An inner surface of the outer member 318a and an outer surface of the inner member 318b define an annular trough channel 318d configured to slidably receive a proximal portion of the coupling portion 312x of the shell 312. The distal collar 319 of the collar assembly 316a includes spokes 319a. The spokes 319a are annularly or radially spaced apart at predetermined arc lengths. The spokes 319a have a collar coupling portion 319b at a proximal end portion thereof that couple to the annular flange 318c of the proximal collar 318 and a ring coupling portion 319c that couple to a ring member 319e at a distal end portion thereof. Each of the spokes 319a includes a first arm 319f, a second arm 319g, and a third arm 319h that are coupled together and disposed at different angles relative to one another. The first and third arms 319f, 319h may be disposed transverse or even perpendicular relative to one another. The ring member 319e of the distal collar 319 is secured to the proximal end portion 316b2 of the staple sheath 316b using any suitable securement technique such as adhesive, welding, fastening, etc. The ring member 319e may be secured to the inner surface 316b8 of the staple sheath 316b.

Figure 7:
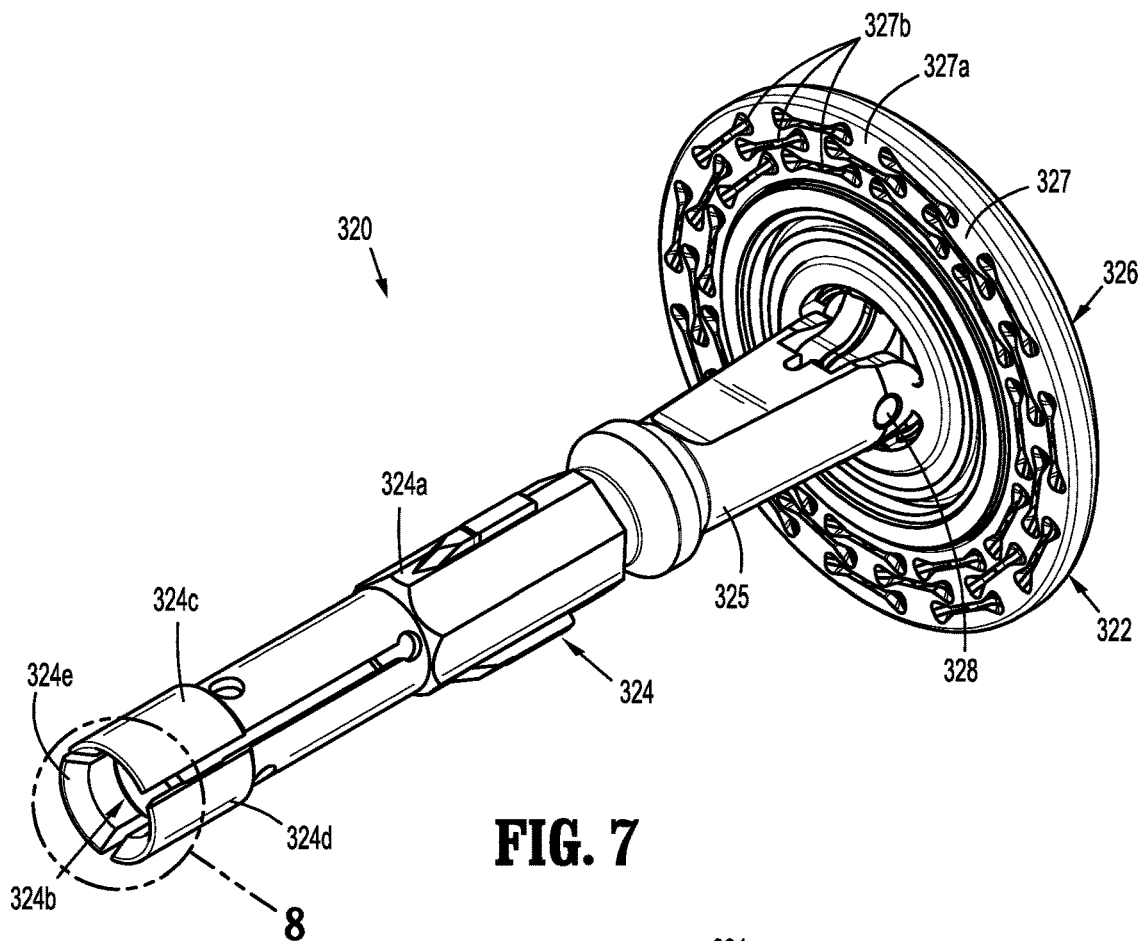
FIG. 7 is a perspective view of the anvil assembly of the end effector of FIG. 2.
Figure 8:
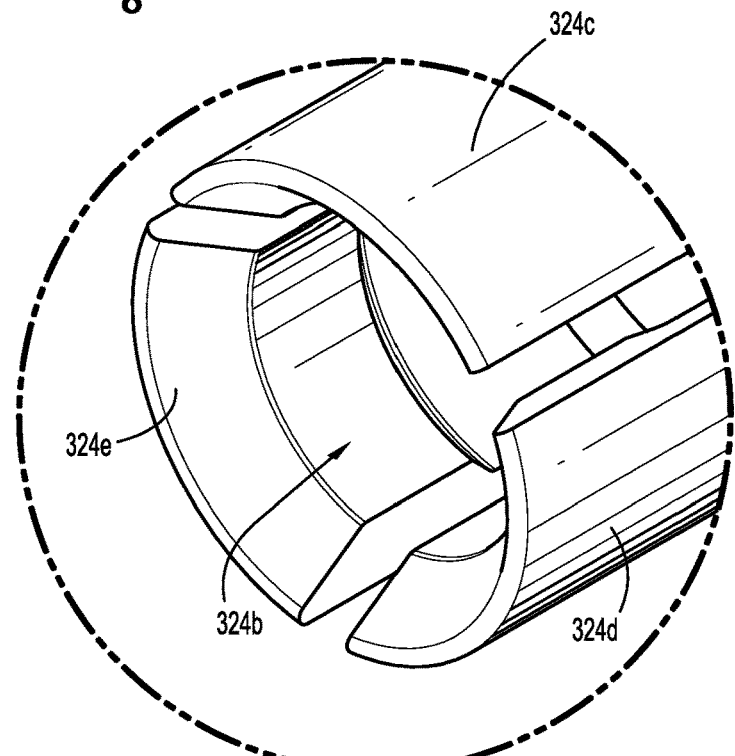
FIG. 8 is an enlarged, perspective view of the indicated area of detail shown in FIG. 7.

With reference to FIGS. 7 and 8, the anvil assembly 320 of the end effector 300 includes an anvil head assembly 322 and an anvil center rod assembly 324. The anvil head assembly 322 includes a post 325, an anvil head 326, and an anvil 327. The anvil 327 of the anvil head assembly 322 is supported on the anvil head 326 of the anvil head assembly 322 and includes a tissue contact surface 327a that defines annular arrays of staple forming pockets 327b arranged to correspond to the annular arrays of slots 315b formed in the staple cartridge 315 of the end effector 300. The annular arrays of pockets 327b of the anvil 317 are arranged to receive and form the staples 317 of the end effector 300 when that staples 317 are ejected or fired from the slots 315b of the staple cartridge 315. The anvil center rod assembly 324 includes an anvil center rod 324a that defines a bore 324b and has flexible arms 324c, 324d, and 324e. The anvil retainer 108a of the approximation mechanism 108 of the electromechanical surgical stapling system 10 is received within the central bore 324b of the anvil center rod 324a such that the flexible or resilient radial arms 324c, 324d, 324e releasably engage the anvil retainer 108a of the approximation mechanism 108 and selectively couple the anvil retainer 108a to the center rod 324a of the anvil assembly 320. A pivot member or pin 328 secures the anvil head assembly 322 to the post 325 to enable the anvil head assembly 322 to pivot relative to the post 325, about the pivot member 328.

Figure 9:
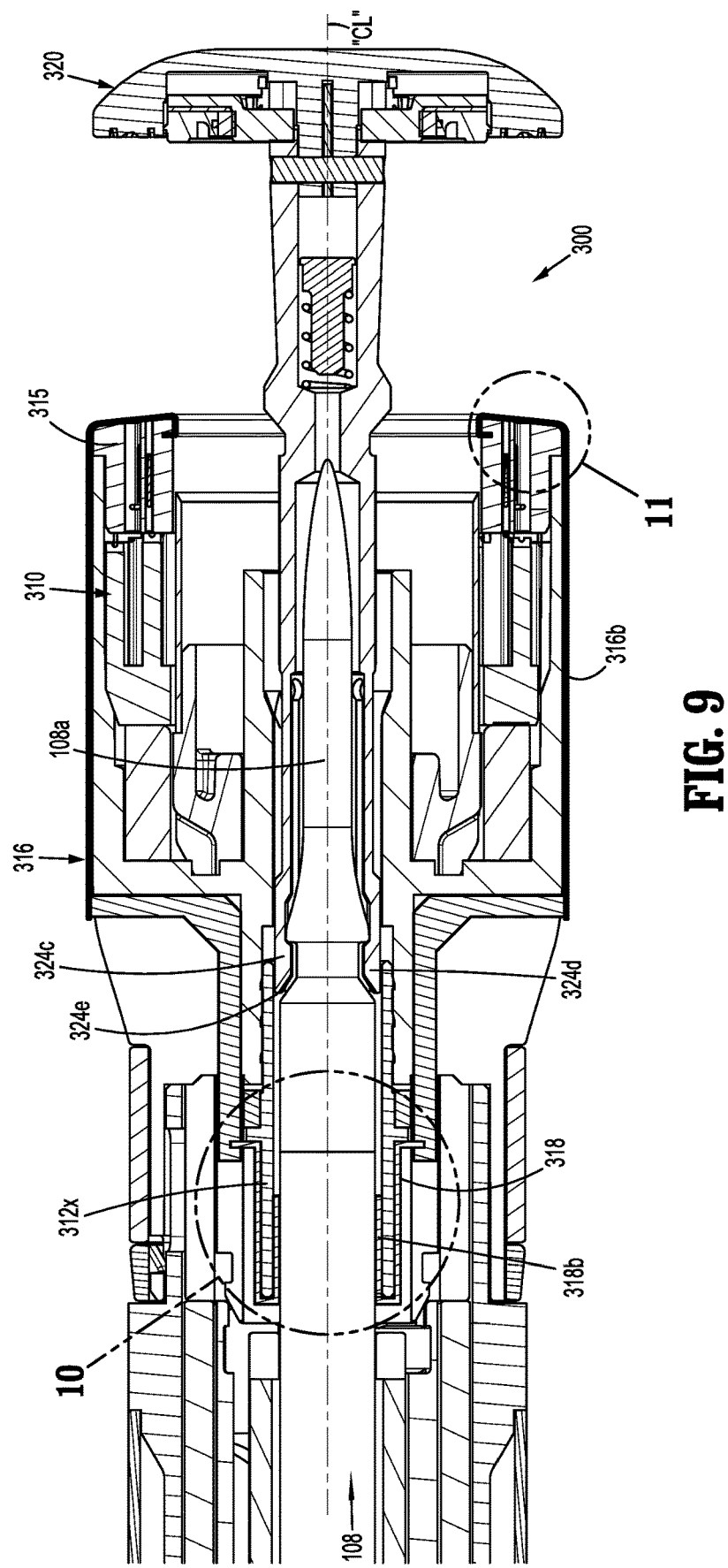
FIG. 9 is a cross-sectional view of the end effector of FIG. 2 as taken along section line 8-8 shown in FIG. 2.
Figure 10:
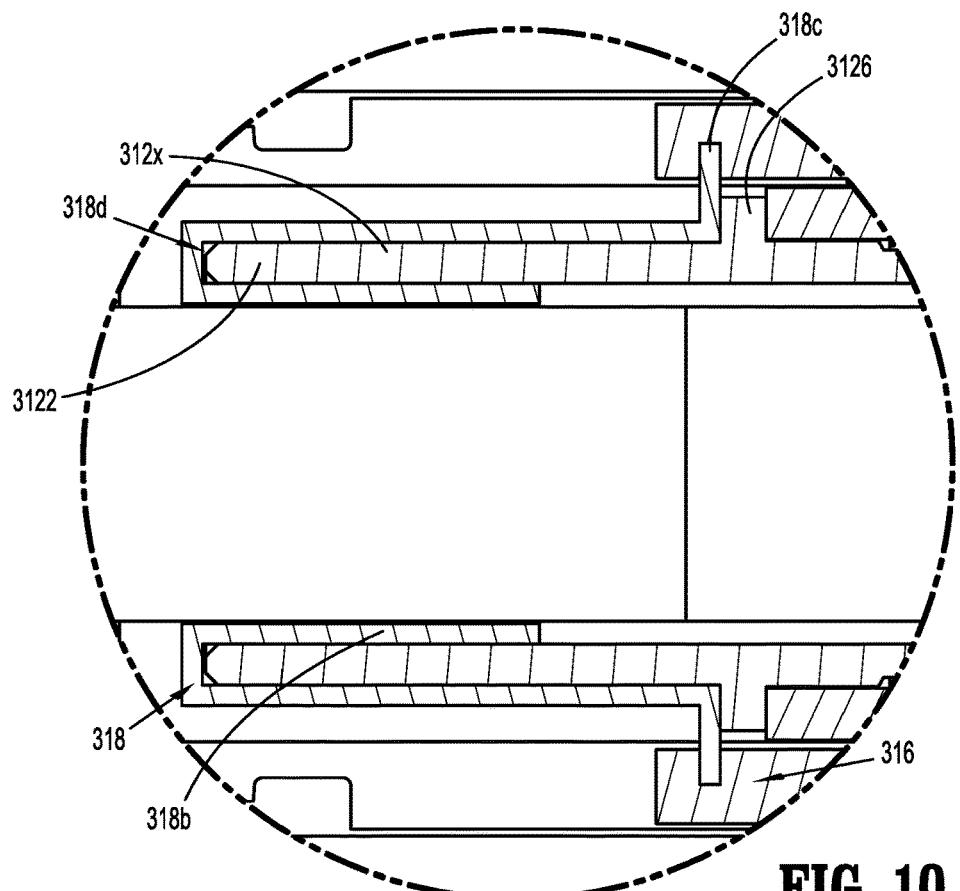
FIGS. 10 and 11 are enlarged, cross-sectional views of the indicated areas of detail shown in FIG. 9, respectively.
Figure 11:
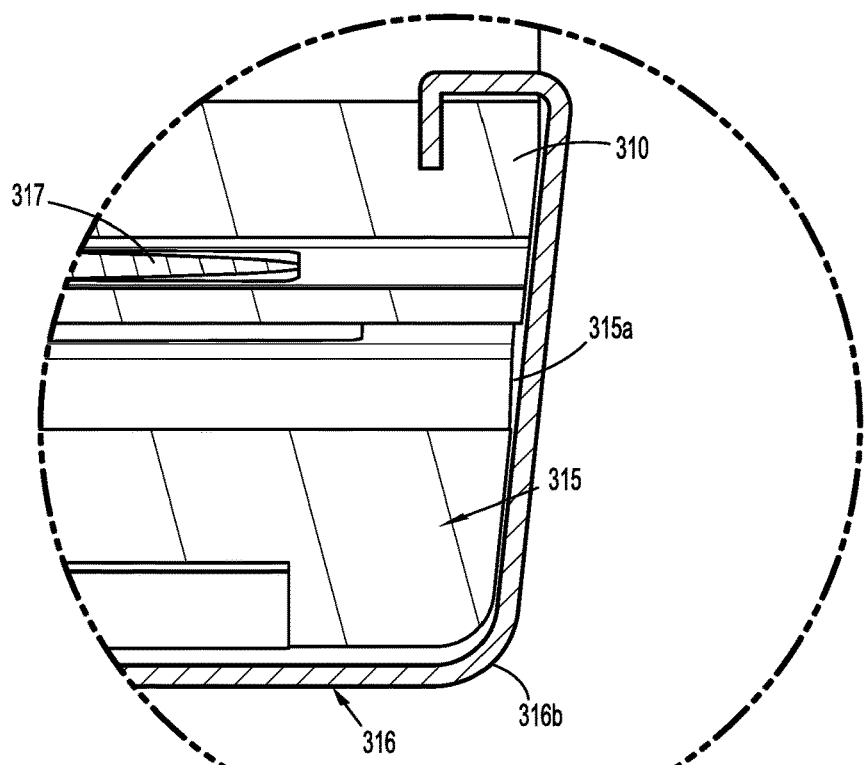

Referring now to FIGS. 9-14, in operation, with the anvil assembly 320 unapproximated from the cartridge assembly 310 and the staple sheath assembly 316 disposed in a distal position, the staple sheath 316b of the staple sheath assembly 316 is secured to the staple cartridge 315 so that the staple sheath 316b covers the staple cartridge 315 (FIGS. 9 and 11). In this distal position of the staple sheath assembly 316, the flexible arms 324c, 324d, 324e of the anvil assembly 320 are longitudinally spaced from the inner member 318b of the proximal collar 318 and the proximal portion 312z2 of the coupling portion 312x of the cartridge assembly 310 is fully seated in the annular trough channel 318d of the proximal collar 318 of the staple sheath assembly 316 such that flange 318c of the proximal collar 318 of the staple sheath assembly 316 and the flange 312b6 of the coupling portion 312x are engaged (FIG. 10). With the staple sheath assembly 316 in the distal position and the end effector 300 in the unapproximated position, the end effector 300 can be advanced to a surgical site with the staples 317 and/or the tissue contact surface 315a of the staple cartridge 315 protected from potential contaminants that could affect sterility of the staples 317 and/or the tissue contact surface 315a of the staple cartridge 315 during advancement to the surgical site (FIG. 11).

Figure 12:
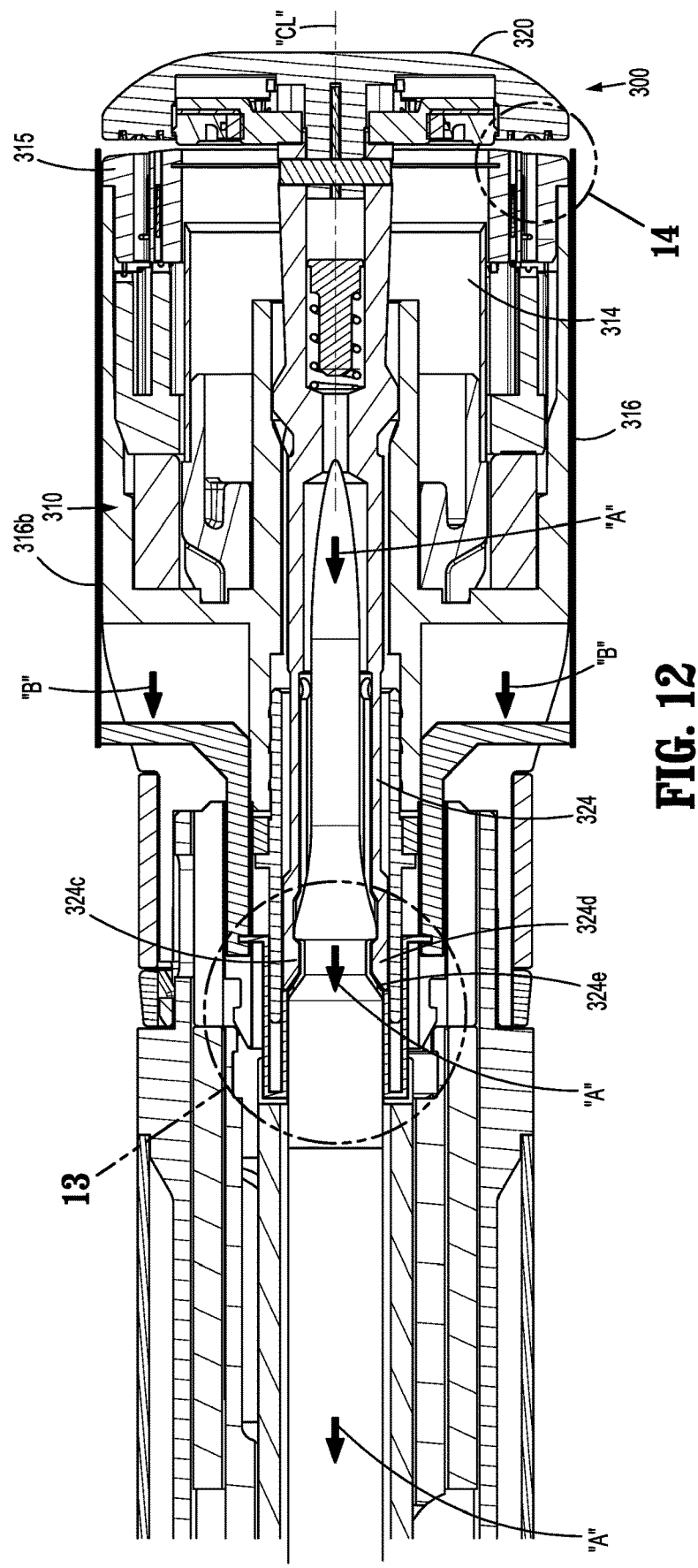
FIG. 12 is a cross-sectional view of the end effector of FIG. 2 as taken along line 8-8 shown in FIG. 2 with the anvil and cartridge assemblies of the end effector shown approximated and with the staple sheath assembly of the cartridge assembly shown in a second position.
Figure 13:
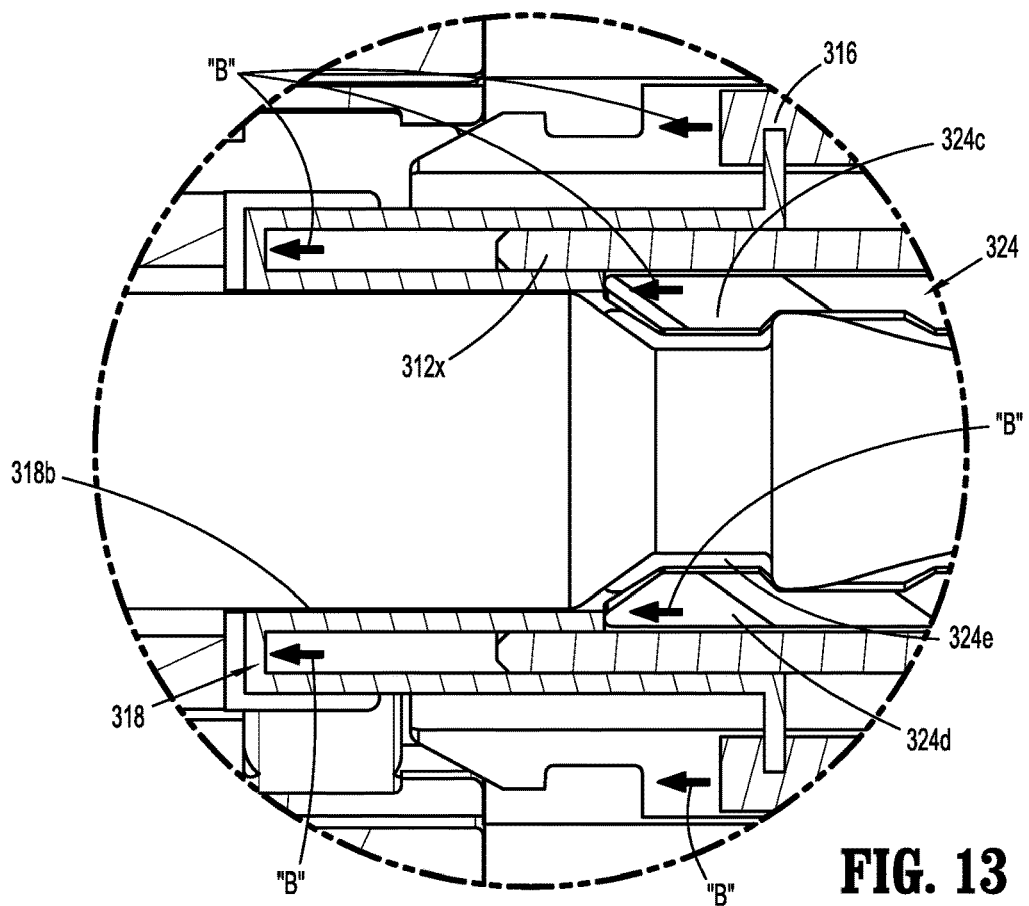
FIGS. 13 and 14 are enlarged, cross-sectional views of the indicated areas of detail shown in FIG. 12, respectively.
Figure 14:
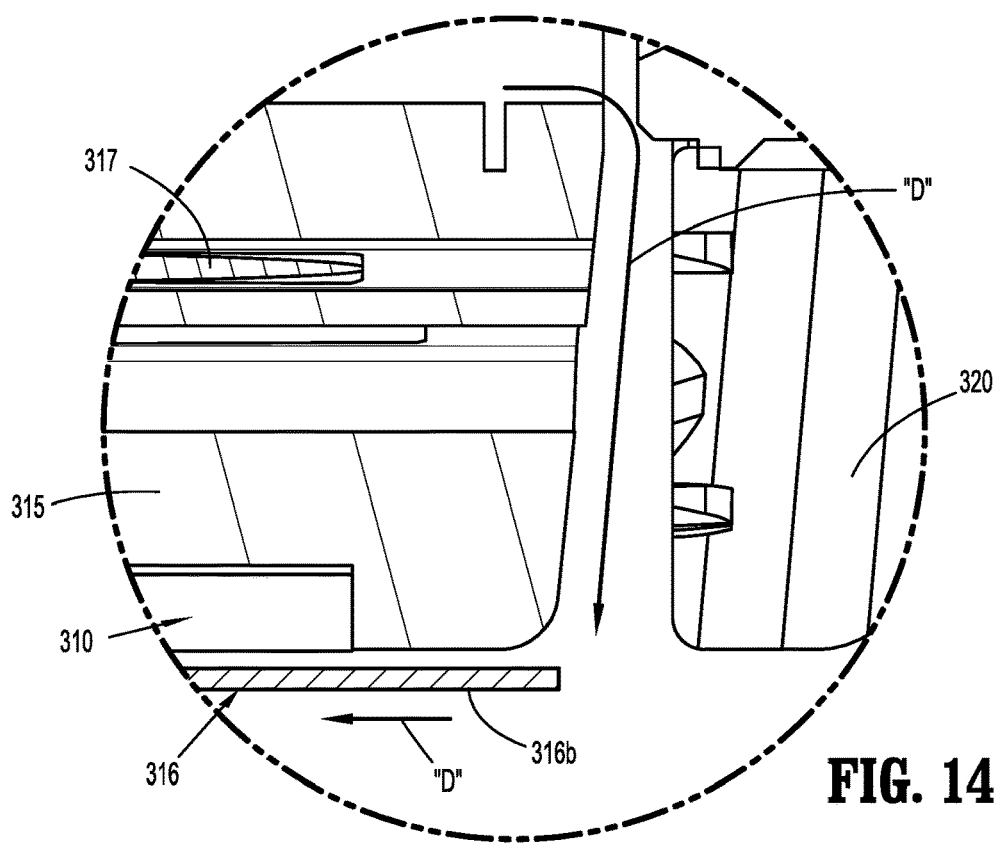

Once the end effector 300 of the electromechanical surgical stapling system 10 is positioned adjacent to the surgical site, the anvil assembly 320 of the end effector 300 can be approximated toward the cartridge assembly 310 of the end effector 300, as indicated by arrows "A" (FIG. 12). As the anvil assembly 320 is approximated toward the cartridge assembly 310, the flexible arms 324c, 324d, 324e of the anvil center rod assembly 324 engage the distal end of the inner member 318b of the proximal collar 318 of the staple sheath assembly 316 and advance or translate the staple sheath assembly 316 proximally, as indicated by arrows "B" (FIGS. 12 and 13). Continued proximal advancement of the staple sheath assembly 316 causes the proximal collar 318 thereof to slide along the coupling portion 312x of the cartridge assembly 310 relative to the centerline "CL" of the electromechanical surgical stapling system 10 (FIG. 1) and causes the staple sheath 316b of the staple sheath assembly 316 to separate from the staple cartridge 315. As the staple sheath assembly 316 moves proximally, the staple sheath 316b thereof draws across the staple cartridge 315, as indicated by arrows "D" (FIG. 14), and exposes the staple cartridge 315 so that once the anvil assembly 320 and the cartridge assembly 310 are approximated to clamp tissue in the end effector 300, the staples 317 can be fired from the cartridge assembly 310 and formed against the anvil assembly 320 (without having to penetrate the staple sheath 316b of the staple sheath assembly 316). The cylindrical knife 314 (FIG. 12) of the cartridge assembly 310 can also be fired to cut the clamped and fastened tissue supported by the end effector 300. For a more detailed description of firing, cutting, and/or fastening of staples, reference can be made to U.S. Pat. No. 7,303,106, incorporated herein by reference above.

Alternatively, or additionally, the staple sheath 316b, or portions thereof, can be configured to enable the staples 317 to be fired therethrough (e.g., such as where the staple sheath 316b, or portions thereof, act as buttress material as described above).

The anvil assembly 320 of the end effector 300 can then be unapproximated or separated from the cartridge assembly 310 of the end effector 300 to release the stapled tissue and remove the end effector 300 from the surgical site. The anvil and/or cartridge assemblies 310, 320 can be removed from the electromechanical surgical stapling system 10 and/or replaced as described in U.S. Pat. No. 7,303,106 and/or U.S. Patent Application Publication No. 2016/0192934, each of which are incorporated herein by reference above.

As can be appreciated, securement of any of the components of the presently disclosed devices can be effectuated using known securement techniques such welding, crimping, gluing, fastening, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely control the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical stapling apparatus, comprising:
a first jaw member having an outer sidewall, an inner sidewall, and a tissue contact surface disposed between the inner and outer sidewalls, the tissue contact surface defining a plurality of staple retention slots;
a plurality of staples, each staple of the plurality of staples received in a respective one of the plurality of staple retention slots;
a second jaw member having a plurality of staple pockets, each staple pocket of the plurality of staple pockets configured to form a respective one of the staples of the plurality of staples as the surgical stapling apparatus is fired, the second jaw member includes a head assembly having a center rod assembly extending proximally from the head assembly; and
a staple sheath having a distal end portion engaged with the tissue contact surface of the first jaw member to cover the plurality of staple retention slots, the distal end portion having a distal end removably secured to the inner sidewall of the first jaw member at a location proximal to the tissue contact surface, the staple sheath movable relative to the first jaw member to uncover the plurality of staple retention slots in response to relative approximation of the first jaw member and the second jaw member, the staple sheath being part of a staple sheath assembly including a collar assembly and the staple sheath coupled to the collar assembly, the center rod assembly selectively engagable with the collar assembly to move the staple sheath relative to the first jaw member to uncover the plurality of staple retention slots in response to relative approximation of the first jaw member and the second jaw member.

2. A surgical stapling apparatus, comprising:
a first jaw member having an outer sidewall, an inner sidewall, and a tissue contact surface disposed between the inner and outer sidewalls, the tissue contact surface defining a plurality of staple retention slots;
a plurality of staples, each staple of the plurality of staples received in a respective one of the plurality of staple retention slots;
a second jaw member having a plurality of staple pockets, each staple pocket of the plurality of staple pockets configured to form a respective one of the staples of the plurality of staples as the surgical stapling apparatus is fired; and
a staple sheath having a distal end portion engaged with the tissue contact surface of the first jaw member to cover the plurality of staple retention slots, the distal end portion having a distal end removably secured to the inner sidewall of the first jaw member at a location proximal to the tissue contact surface, the staple sheath movable relative to the first jaw member to uncover the plurality of staple retention slots in response to relative approximation of the first jaw member and the second jaw member, the staple sheath being part of a staple sheath assembly including a collar assembly and the staple sheath coupled to the collar assembly, the collar assembly including at least one spoke and the first jaw member defining at least one elongated channel that extends axially along the first jaw member, the at least one spoke slidably movable through the at least one elongated channel to enable the staple sheath to move relative to the first jaw member.

3. The surgical stapling apparatus of claim 1, wherein the first jaw member includes a staple cartridge that defines the outer sidewall and the inner sidewall, the staple cartridge defining an annular groove in the inner sidewall, the annular groove configured to receive the distal end of the staple sheath assembly to selectively secure the staple sheath across the staple cartridge covering the plurality of staple retention slots while the first and second jaw members are unapproximated.

4. The surgical stapling apparatus of claim 1, further comprising an elongated shaft assembly that extends from a proximal end portion to a distal end portion, the first jaw member and the staple sheath assembly removably secured to the distal end portion of the elongated shaft assembly.

5. An end effector for a surgical stapling apparatus, the end effector comprising:
a cartridge assembly having an inner sidewall and a tissue contact surface, the cartridge assembly defining a plurality of staple retention slots that extends along the inner sidewall and through the tissue contact surface;
a plurality of staples, each staple of the plurality of staples received in a respective one of the plurality of staple retention slots;
an anvil assembly having a plurality of staple pockets, each staple pocket of the a plurality of staple pockets configured to form a respective one of the staples of the plurality of staples as the surgical stapling apparatus is fired, the anvil assembly movable relative to the cartridge assembly between an unapproximated position and an approximated position, the anvil assembly including a head assembly and a center rod assembly that extends from the head assembly; and
a staple sheath having a distal end portion engaged with the tissue contact surface of the cartridge assembly and positioned to cover the plurality of staple retention slots, the distal end portion having a distal end received within and removably secured to the cartridge assembly at a location along the inner sidewall of the cartridge assembly that is proximal to the tissue contact surface of the cartridge assembly, the staple sheath movable with the anvil assembly to uncover the plurality of staple retention slots and expose the plurality of staples, the staple sheath being part of a staple sheath assembly including a collar assembly and the staple sheath coupled to the collar assembly, the center rod assembly selectively engagable with the collar assembly to move the staple sheath relative to the cartridge assembly upon a movement of the anvil assembly relative to the cartridge assembly.

6. An end effector for a surgical stapling apparatus, the end effector comprising:
a cartridge assembly having an inner sidewall and a tissue contact surface, the cartridge assembly defining a plurality of staple retention slots that extends along the inner sidewall and through the tissue contact surface;
a plurality of staples, each staple of the plurality of staples received in a respective one of the plurality of staple retention slots;
an anvil assembly having a plurality of staple pockets, each staple pocket of the a plurality of staple pockets configured to form a respective one of the staples of the plurality of staples as the surgical stapling apparatus is fired, the anvil assembly movable relative to the cartridge assembly between an unapproximated position and an approximated position; and
a staple sheath having a distal end portion engaged with the tissue contact surface of the cartridge assembly and positioned to cover the plurality of staple retention slots, the distal end portion having a distal end received within and removably secured to the cartridge assembly at a location along the inner sidewall of the cartridge assembly that is proximal to the tissue contact surface of the cartridge assembly, the staple sheath movable with the anvil assembly to uncover the plurality of staple retention slots and expose the plurality of staples, the staple sheath being part of a staple sheath assembly including a collar assembly and the staple sheath coupled to the collar assembly, the collar assembly including at least one spoke and the cartridge assembly defining at least one elongated channel extending axially along the cartridge assembly, the at least one spoke slidably movable through the at least one elongated channel to enable the staple sheath to move relative to the cartridge assembly.

7. The end effector of claim 5, wherein the cartridge assembly includes a staple cartridge defining an annular groove configured to receive the distal end of the staple sheath assembly to selectively secure the staple sheath in a position to cover the plurality of staple retention slots while the anvil and cartridge assemblies are in the unapproximated position.

8. The end effector of claim 5, further comprising an elongated shaft assembly that extends from a proximal end portion to a distal end portion, the cartridge assembly and the staple sheath assembly removably secured to the distal end portion of the elongated shaft assembly.

9. A circular stapling apparatus, comprising:
an elongated shaft assembly having a distal end portion and defining a longitudinal axis;
a cartridge assembly secured to the distal end portion of the elongated shaft assembly, the cartridge assembly having an inner sidewall and having a tissue contact surface, the tissue contact surface defining a plurality of staple retention slots;
a plurality of staples, each staple of the plurality of staples received in a respective one of the plurality of staple retention slots;
a collar assembly movable along the longitudinal axis between a distal position and a proximal position; and
a staple sheath having a distal end portion engaged with the tissue contact surface of the cartridge assembly and a proximal end portion coupled to the collar assembly, the distal end portion positioned to cover the plurality of staple retention slots while the collar assembly is in the distal position, the distal end portion including a distal end received within and secured to the cartridge assembly when the collar assembly is in the distal position, the distal end secured to the inner sidewall of the cartridge assembly proximal to the tissue contact surface of the cartridge assembly, the staple sheath movable with the collar assembly toward the proximal position to separate the distal end of the staple sheath from the cartridge assembly and draw the distal end of the staple sheath across the plurality of staple retention slots, the collar assembly including at least one spoke and the cartridge assembly defining at least one elongated channel extending axially along the cartridge assembly, the at least one spoke slidably movable through the at least one elongated channel to enable the staple sheath to move relative to the cartridge assembly.

10. The circular stapling apparatus of claim 9, wherein the cartridge assembly includes a staple cartridge defining an annular groove configured to receive the distal end of the staple sheath to selectively secure the staple sheath in a position to cover the plurality of staple retention slots.

11. The circular stapling apparatus of claim 9, wherein the cartridge assembly and the staple sheath assembly are selectively removable from the distal end portion of the elongated shaft assembly.

12. The circular stapling apparatus of claim 9, further comprising an anvil assembly selectively coupled to the elongated shaft assembly, the anvil assembly movable relative to the cartridge assembly to move the collar assembly from the distal position to the proximal position.

13. A cartridge assembly for selective connection to a surgical stapling apparatus, the cartridge assembly comprising:
a body portion having an inner sidewall defining a central opening therethrough, the body portion defining at least one elongated channel;
a tissue contact surface defining a plurality of staple retention slots;
a plurality of staples, each staple of the plurality of staples received in a respective one of the plurality of staple retention slots;
a collar assembly movably mounted to the body portion, the collar assembly including at least one spoke; and
a staple sheath having a proximal end portion coupled to the collar assembly and a distal end portion positioned to cover the plurality of staple retention slots, the distal end portion received within the central opening and having a distal end connected to the inner sidewall of the body portion at a location proximal to the tissue contact surface, the staple sheath selectively movable relative to the tissue contact surface to disconnect the distal end portion from the body portion, the at least one spoke slidably movable through the at least one elongated channel to enable the staple sheath to move relative to the body portion.

14. The cartridge assembly of claim 13, further comprising a staple cartridge coupled to the body portion, the staple cartridge including the tissue contact surface and supporting the plurality of staples, and wherein the staple cartridge defines an annular groove configured to receive the distal end of the staple sheath to selectively secure the staple sheath across the tissue contact surface of the staple cartridge.

* * * * *